(12) United States Patent
Palmerton et al.

(10) Patent No.: US 9,532,843 B2
(45) Date of Patent: Jan. 3, 2017

(54) MEDICAL BOOM FILTER SYSTEM AND METHOD

(71) Applicant: MEDTEK DEVICES, INC., Buffalo, NY (US)

(72) Inventors: Christopher A. Palmerton, Clarence, NY (US); Samantha Bonano, Williamsville, NY (US); Anthony Lizauckas, Williamsville, NY (US); Kyrylo Shvetsov, Tonawanda, NY (US); Daniel Palmerton, Elma, NY (US); Gregory Pepe, Lancaster, NY (US); Joseph Lynch, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 53 days.

(21) Appl. No.: 14/377,850

(22) PCT Filed: Feb. 14, 2013

(86) PCT No.: PCT/US2013/026149
§ 371 (c)(1),
(2) Date: Aug. 9, 2014

(87) PCT Pub. No.: WO2013/123196
PCT Pub. Date: Aug. 22, 2013

(65) Prior Publication Data
US 2015/0013783 A1   Jan. 15, 2015

Related U.S. Application Data

(60) Provisional application No. 61/640,206, filed on Apr. 30, 2012, provisional application No. 61/598,645, filed on Feb. 14, 2012.

(51) Int. Cl.
*B01D 24/00* (2006.01)
*A61B 19/00* (2006.01)
(Continued)

(52) U.S. Cl.
CPC ............... *A61B 19/26* (2013.01); *A61B 90/50* (2016.02); *B01D 46/0036* (2013.01);
(Continued)

(58) Field of Classification Search
CPC ............ B01D 2257/90; B01D 2257/91; B01D 2253/102; B01D 53/04; B01D 46/4236; B01D 46/0036; A61B 90/50; A61B 2217/005; A61B 2218/007; Y10T 137/6966
(Continued)

(56) References Cited

U.S. PATENT DOCUMENTS

| 4,038,913 A | 8/1977 | Earley |
| 4,158,462 A | 6/1979 | Coral |

(Continued)

FOREIGN PATENT DOCUMENTS

WO    02/060314 A2    8/2002

*Primary Examiner* — Marina Tietjen
*Assistant Examiner* — Umashankar Venkatesan
(74) *Attorney, Agent, or Firm* — Michael J. Berchou, Esq.; Timothy W. Menasco, Esq.; Harter Secrest & Emery LLP

(57) ABSTRACT

A surgical boom having a surgical head with an electrical connection, a plurality of inlet ports, a compressed gas outlet, and a water outlet, one of the inlet ports having a cover, a hollow surgical arm mounted to a ceiling in a room and having a plurality of joints, a shaft passing through said ceiling, and a shaft collar attached to the ceiling, an outlet port, a filter media arranged between said outlet port and one of the inlet ports, the filter media comprising an ULPA media and an adsorbant layer, a control panel, a suction unit
(Continued)

configured and arranged in a position below the ceiling to cause a fluid to be drawn from the inlet port through the filter media and out through said outlet port while minimizing noise in the proximity of the inlet port, wherein the fluid drawn from said inlet port comprises an exhaust path through the hollow arm.

8 Claims, 7 Drawing Sheets

(51) Int. Cl.
  *B01D 46/00* (2006.01)
  *B01D 46/42* (2006.01)
  *B01D 53/04* (2006.01)
(52) U.S. Cl.
  CPC .... *B01D 46/4236* (2013.01); *A61B 2217/005* (2013.01); *A61B 2218/007* (2013.01); *B01D 53/04* (2013.01); *B01D 2253/102* (2013.01); *B01D 2257/90* (2013.01); *B01D 2257/91* (2013.01); *Y10T 137/6966* (2015.04)
(58) Field of Classification Search
  USPC .............. 55/385.1, 385.2, 467, 473; 137/615
  See application file for complete search history.

(56) References Cited

U.S. PATENT DOCUMENTS

| | | | |
|---|---|---|---|
| 4,786,295 A | 11/1988 | Newman et al. | |
| 4,963,134 A | 10/1990 | Backscheider et al. | |
| 5,047,072 A | 9/1991 | Wertz et al. | |
| 5,087,198 A * | 2/1992 | Castellini | A61C 1/0038 433/28 |
| 5,096,474 A | 3/1992 | Miller, Jr. et al. | |
| 5,192,424 A | 3/1993 | Beyne et al. | |
| 5,226,939 A | 7/1993 | Nicolas et al. | |
| 5,242,474 A | 9/1993 | Herbst et al. | |
| 5,264,026 A | 11/1993 | Paul | |
| 5,318,516 A | 6/1994 | Cosmescu | |
| 5,409,511 A | 4/1995 | Paul | |
| 5,507,847 A | 4/1996 | George et al. | |
| 5,531,802 A | 7/1996 | Schlor et al. | |
| 5,597,385 A | 1/1997 | Moerke | |
| 5,636,627 A | 6/1997 | Rochester | |
| 5,702,493 A | 12/1997 | Everetts et al. | |
| 5,709,675 A | 1/1998 | Williams | |
| 5,715,813 A | 2/1998 | Guevrekian | |
| 5,738,148 A | 4/1998 | Coral et al. | |
| 5,785,723 A | 7/1998 | Beran et al. | |
| 5,853,410 A | 12/1998 | Greff et al. | |
| 5,904,896 A | 5/1999 | High | |
| 5,914,415 A | 6/1999 | Tago | |
| 5,941,873 A | 8/1999 | Korenfeld | |
| 6,045,596 A | 4/2000 | Holland, Jr. et al. | |
| 6,053,886 A * | 4/2000 | Holland, Jr. | A61B 18/00 604/118 |
| 6,093,229 A | 7/2000 | Lee et al. | |
| 6,099,607 A | 8/2000 | Haslebacher | |
| 6,143,048 A | 11/2000 | Comproni et al. | |
| 6,180,000 B1 | 1/2001 | Wilbur et al. | |
| 6,203,590 B1 * | 3/2001 | Byrd | B01D 46/0023 55/319 |
| 6,308,707 B1 | 10/2001 | Lu | |
| 6,332,308 B1 | 12/2001 | Miller | |
| 6,334,881 B1 | 1/2002 | Giannetta et al. | |
| 6,369,353 B1 | 4/2002 | Soska | |
| 6,395,047 B1 | 5/2002 | Smith | |
| 6,497,738 B2 | 12/2002 | Lin | |
| 6,524,307 B1 | 2/2003 | Palmerton et al. | |
| 6,544,210 B1 | 4/2003 | Trudel et al. | |
| 6,551,185 B1 | 4/2003 | Miyake et al. | |
| 6,553,613 B2 | 4/2003 | Onishi et al. | |
| 6,558,444 B1 | 5/2003 | Hunter | |
| 6,660,070 B2 | 12/2003 | Chung et al. | |
| 6,755,734 B2 | 6/2004 | Yokoyama et al. | |
| 7,153,347 B2 | 12/2006 | Kang et al. | |
| 7,597,731 B2 | 10/2009 | Palmerton et al. | |
| 7,621,978 B2 | 11/2009 | Johansson | |
| 7,892,337 B2 * | 2/2011 | Palmerton | A61B 18/00 55/385.1 |
| 2003/0035737 A1 * | 2/2003 | Ishikawa | F04D 19/04 417/309 |
| 2003/0129936 A1 | 7/2003 | Shaikh | |
| 2005/0060974 A1 * | 3/2005 | Palmerton | A61B 18/00 55/482 |
| 2009/0288561 A1 | 11/2009 | Palmerton et al. | |

* cited by examiner

MEDICAL BOOM FILTER SYSTEM AND METHOD

CROSS-REFERENCE TO RELATED APPLICATIONS

The present application claims priority from U.S. provisional application No. 61/598,645 filed on Feb. 14, 2012 and U.S. provisional application No. 61/640,206 filed on Apr. 30, 2012, of which both applications are hereby incorporated by reference in their entirety.

BACKGROUND OF THE INVENTION

The present invention relates generally to filters and more specifically to low noise filter systems integrated in a medical boom. U.S. Pat. No. 6,045,596 is directed to a filter system self contained within a treatment room and having a portion of which incorporated into a surgical arm, the aggregate disclosure of which is hereby incorporated by reference in its entirety. U.S. Pat. No. 7,597,731 is directed to an operating room smoke evacuator which is mounted to a medical boom, the aggregate disclosure of which is hereby incorporated by reference in its entirety. U.S. Provisional Application No. 61/431,492, filed Jan. 11, 2011 and U.S. Provisional Application No. 61/579,937, filed Dec. 23, 2011 are directed to a automatically activate remote control system that can be used with a filter system, each of which are hereby incorporated by reference in their entirety.

BRIEF SUMMARY OF THE INVENTION

With reference to the corresponding parts portions or surfaces of the disclosed embodiment, merely for the purposes of illustration and not by way of limitation, a filter system (110) is provided comprising of: a surgical head (31) having a control panel (32) and an inlet port (10); a hollow surgical arm (46) mounted to a ceiling (C) and having a shaft (61) extending through the ceiling and a collar (62) mounted to the ceiling; a filter media (11); an outlet port (66); and a suction unit (51) mounted to the shaft and configured and arranged to cause a fluid to be drawn from said inlet port, through the filter media, and out through the outlet port whereby noise in the proximity of said inlet port is minimized.

In another aspect, a filter system (210) is provided comprising of: a surgical head (31) having a control panel (32) and an inlet port (10); a hollow surgical arm (46) mounted to a ceiling (C) and having a shaft (61) extending through the ceiling and a collar (62) mounted to the ceiling; a filter media (11); an outlet port (66); and a suction unit (51) mounted to the collar and configured and arranged to cause a fluid to be drawn from said inlet port, through the filter media, and out through the outlet port whereby noise in the proximity of said inlet port is minimized. The control panel may be on the surgical head or arranged at a remote location from the surgical head.

In another aspect, a filter system (310) is provided comprising of: a surgical head (31) having a control panel (32) and an inlet port (10); a hollow surgical arm (46) mounted to a ceiling (C) and having a shaft (61) extending through the ceiling and a collar (62) mounted to the ceiling; a filter media (11); an outlet port (66); and a suction unit (51) mounted to the to the shaft above the ceiling and configured and arranged to cause a fluid to be drawn from said inlet port, through the filter media, and out through the outlet port whereby noise in the proximity of said inlet port is minimized.

In another aspect, a filter system (410) is provided comprising of: a surgical head (31) having a control panel (32) and an inlet port (10); a hollow surgical arm (46) mounted to a ceiling (C) and having a shaft (61) extending through or along the ceiling and a collar (62) mounted to the ceiling; a filter media (11); an outlet port (66) exhausting into the ceiling; and a suction unit (51) mounted within the surgical head and configured and arranged to cause a fluid to be drawn from said inlet port, through the filter media, and out through the outlet port whereby noise in the proximity of said inlet port is minimized.

The outlet port may extend through the ceiling.

The surgical arm may contain several joints. The joints may have roller bearings. The arm may be mass balanced about each joint. The arm may have a torsional spring mounted at a joint to counteract gravitational forces acting on the joint. The surgical arm may contain an active brake configured and arranged to prevent joints of the arm from moving. The arm joints may be powered with a motor.

The suction unit may be a vacuum motor or other similar vacuum device. The vacuum motor may be an impeller, a fan, or a pump. The suction unit may contain vibration isolating or absorbing material (56) or a vibration isolating or absorbing housing mount (57).

The filter media may contain multiple layers. The filter media may contain a prefilter layer, a hydrophobic layer, and an odor absorbing later. The filter media may be a ULPA filter, a HEPA filter, or a fiber filter. The filter media may contain activated charcoal, polyester, or PTFE. The filter media may contain an antimicrobial material. The filter media may contain an RFID tag and the RFID tag may contain filter type and lifetime information. The RFID tag may be writable and the system may be configured to write updated lifetime information after each use. The filter may contain a one way valve.

The service head may have an electrical connection and may provide electrical outlets. The service head may receive compressed gas and may provide a compressed gas outlet. The service head may receive water and may provide a water outlet. The control panel may contain a display. The display may be on the service head or arranged at a location remote to the service head. The service head may contain a plurality of inlet ports. The inlet ports may contain port flaps and the port flaps may contain flexible covers. The flexible covers may contain adhesive material for holding the covers in place. The adhesive material may be magnetic material The system may have a liquid trap or a liquid exit port.

The system may contain a valve configured and arranged to control fluid flow through the filter. The valve may be a solenoid valve and may have a biased default position. The biased default position may be a closed position.

The system may contain a remote control. The system may contain an automatic activation controller. The automatic activation controller may be activated by sound, radio energy, a current sensor, or an electrosurgical device outlet. The automatic activation controller may be voice activated.

In another aspect, a remote control unit is provided comprising: a receiver having an output; an output control line for controlling a device; a threshold parameter storage; an integrated antenna; a controller; wherein the controller may be configured to produce a signal on the output control line as a function of the receiver output and the threshold parameter storage.

In another aspect, a filter system (510) is provided comprising of: a surgical head (31) having a control panel (32) and an inlet port (10); a hollow surgical arm (46) mounted to a ceiling (C) and having a shaft (61) extending through the ceiling and a collar (62) mounted to the ceiling; a filter media (11); an outlet port (66) exhausting into the ceiling; and a suction unit (551a) arranged within the ceiling adjacent to the outlet port and configured and arranged to cause a fluid to be drawn from said inlet port, through the filter media, and out through the outlet port whereby noise in the proximity of said inlet port is minimized.

The suction unit may also be arranged (551b) within the collar (62). The suction unit may also be arranged (551c) within an upper portion of the shaft (61a). The suction unit may also be arranged (551d) within a lower portion of the shaft (61b). The suction unit may also be arranged (551e) within a central region of a horizontal linkage portion (44) of the surgical arm. The suction unit may also be arranged (551f) within a proximal region of a horizontal linkage portion (44) of the surgical arm. The suction unit may also be arranged (551g) within a cylindrical joint section (46) of the surgical arm. The suction unit may also be arranged (551h) within an angled descending linkage portion (45) of the surgical arm.

In another aspect, an RFID reader and tag pair may be arranged at every coupling of the system. In another aspect suction for fluid management with controls on the boom may be provided. In another aspect, air may be exhausted out of the boom for warming.

DETAILED DESCRIPTION OF THE INVENTION

Figure 1:
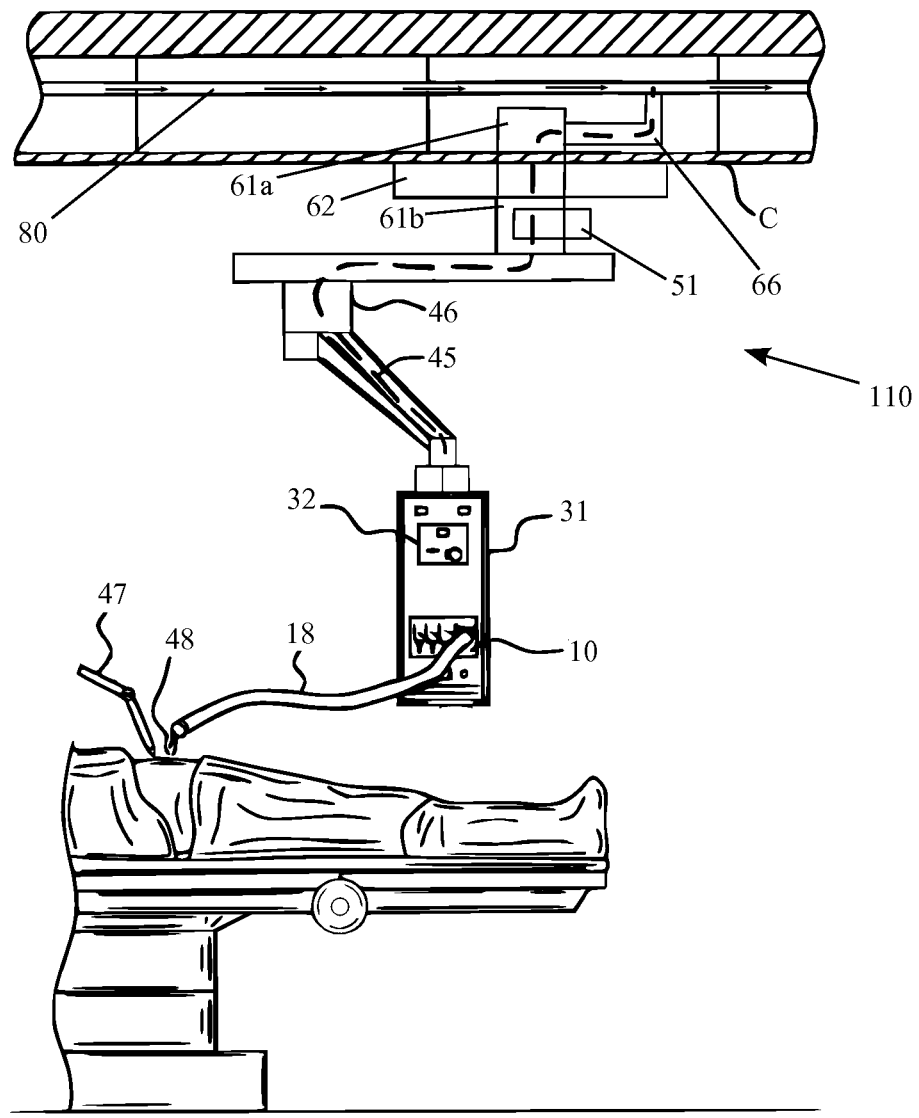
FIG. 1 shows a side view of a first embodiment filter system.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, FIG. 1 discloses first embodiment 110 of a filter system. Filter system 110 generally contains hollow surgical arm 46, arm mounting shaft 61 extending into ceiling C, arm collar 62, suction unit 51 mounted to shaft 61, and surgical head 31 mounted on the end of arm 46.

Surgical arm 46 has a hollow passageway for passage of gas, liquid, electrical lines, and control lines. Surgical arm 46 contains four segments connected to each other through three rotary joints. Collar 62 and mounting shaft 61 are rigidly connected to each other and together form the first segment. Collar 62 and mounting shaft 61 are mechanically coupled to ceiling C. Mounting shaft 61 extends through ceiling C and contains upper portion 61a within the ceiling and lower portion 61b which extends below ceiling C and through collar 62. Arm 46 second segment is coupled to shaft lower portion 61b through a rotary joint. Arm 46 third segment is coupled to the second segment through a rotary joint, and arm 46 fourth segment is coupled to the third segment through a rotary joint. Surgical head 31 is mounted at the end of the fourth segment of arm 46 also through a rotary joint.

Each of the rotary joints are arranged for movement about a vertical axis. The rotary joints are low friction roller bearings. Along each joint is an electrical brake for locking the joint. The brake is biased to be locked in the absence of electrical power. The brake may be opened with the application of constant electrical power to allow the joint to move.

Several lines pass from ceiling C through surgical arm 46 to surgical head 31 including a compressed gas line, a water line, electrical power lines, and vacuum line 45. Surgical head 31 has control panel 32 and inlet port 10. Control panel 32 has standard electrical outlets for connection of medical equipment. Inlet port 10 is made up of four inlets. Each inlet has a flexible cover with magnetic material for holding the cover over the inlet. The inlets are configured for receiving standard inlet tube 18.

Figure 4:
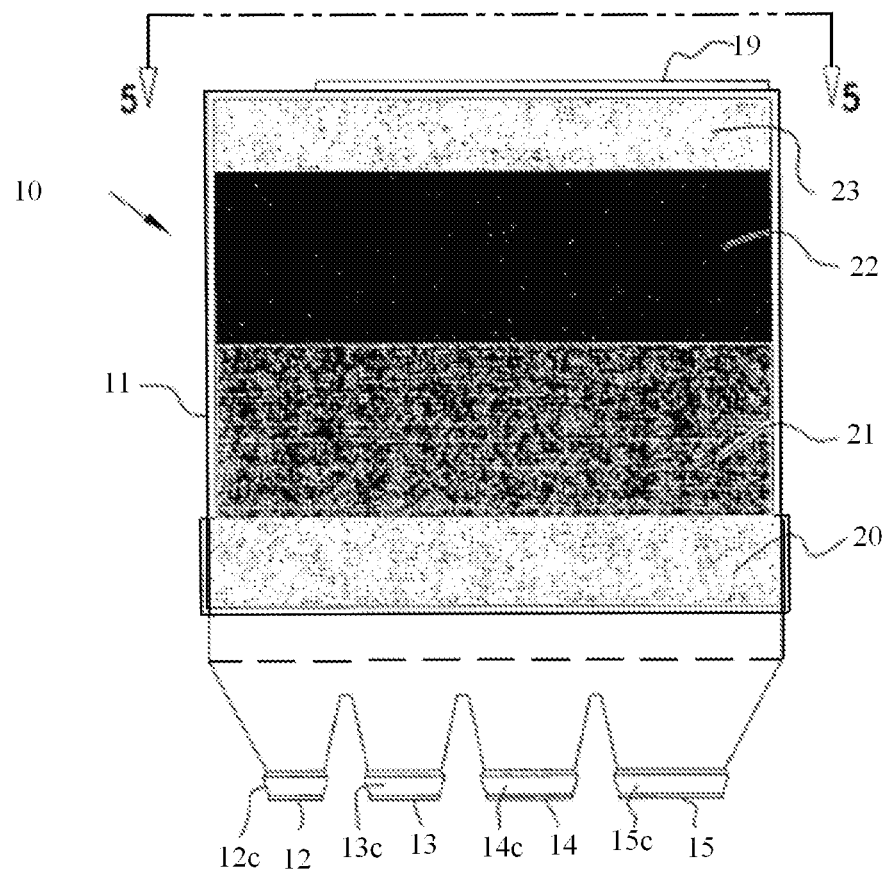
FIG. 4 is a section view of a filter media.

Filter media 11 is arranged within surgical head 31 interior to inlet port 10. As shown in FIG. 4, filter media 11 is made up of several layers. Prefilter layer 20 is configured to trap and retain particles from smoke of other vapors. Prefilter layer 20 is made from polyester fibers. A hydrophobic material may also be used for prefilter layer 20 such as expanded PTFE membrane. Second filter layer 21 is a ULPA material. Second filter layer 21 may contain antimicrobial material. Activated carbon layer 22 contains activated charcoal and is configured to trap gases, odors, organic vapors, and toxins. Post filter layer 23 is melt blown polypropylene.

Figure 5:
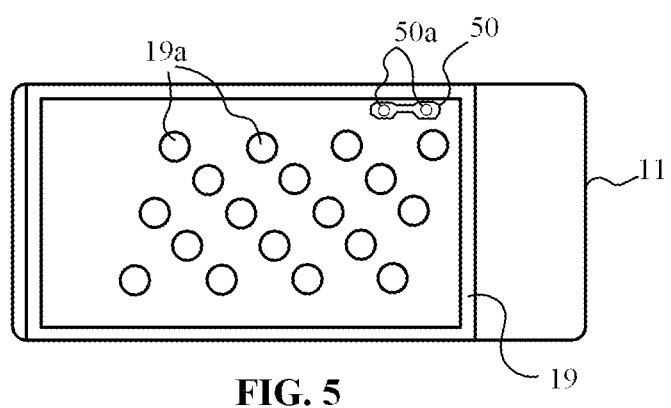
FIG. 5 is a side view of a filter media cover.

FIG. 5 is a rear view of filter media 11 showing a plurality of outlets 19a surrounded by gasket 19. A writable RFID tag is embedded on filter media 11. Writable RFID tag contains filter information such as filter type, id number, and remaining filter lifetime. Surgical head 31 contains a RFID reader/writer which is arranged to read the RFID tag on filter media 11. Surgical head 31 contains a controller that monitors filter usage and updates the RFID tag's remaining lifetime information. Surgical head 31's controller will provide a warning to a user if the remaining lifetime is approaching zero.

Figure 6:
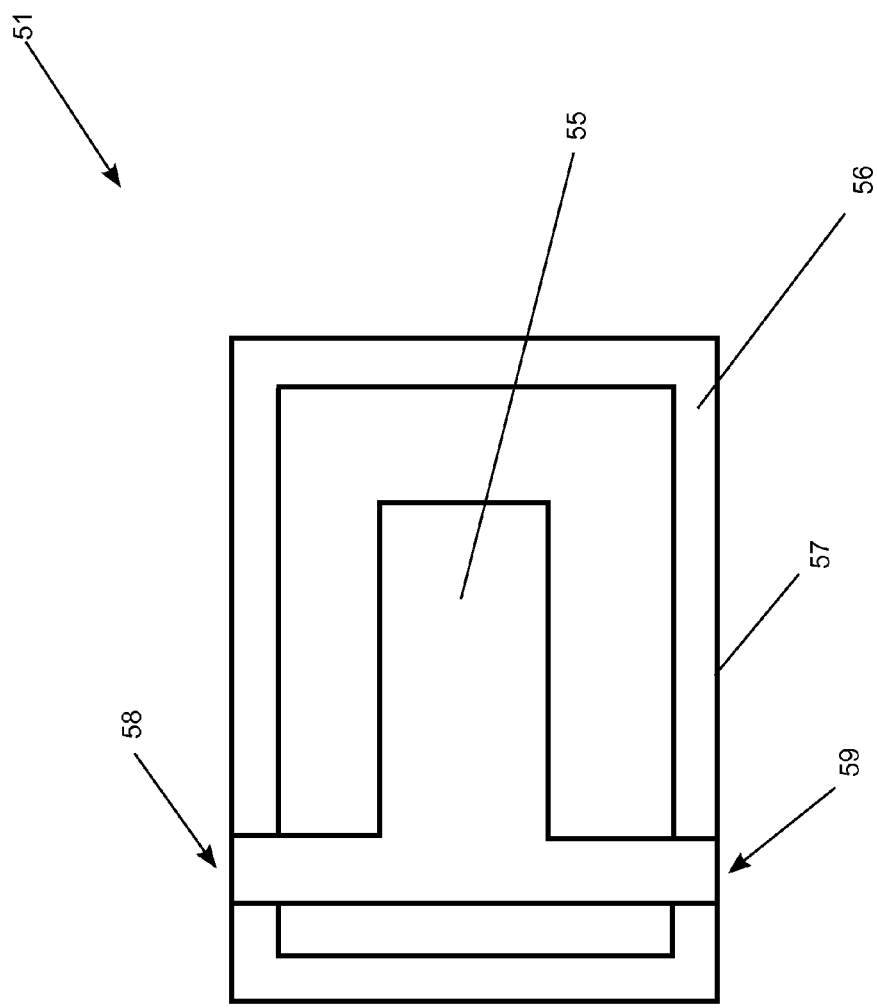
FIG. 6 is a section view of a suction unit.

Suction unit 51 is arranged on mounting lower portion 61b as shown in FIG. 1. FIG. 6 is a section view of suction unit 51. Suction unit 51 contains inlet 59, outlet 58, and vacuum motor 55. Vacuum motor 55 may be an impeller, vacuum pump, fan, or other similar vacuum device. Suction unit 51 contains vibration absorbing and isolating material 56. Material 56 contains neoprene and foam, but may be comprised of other similar materials. Suction unit 51 also contains housing mount 57 which is optimized for absorbing vibration and minimizing vibration transfer to surgical arm 46. Housing mount 57 is made from rubber.

As shown in FIG. 1, suction unit 51 exhausts though exhaust line 66 which exhaust into ceiling exhaust line 80.

Figure 2:
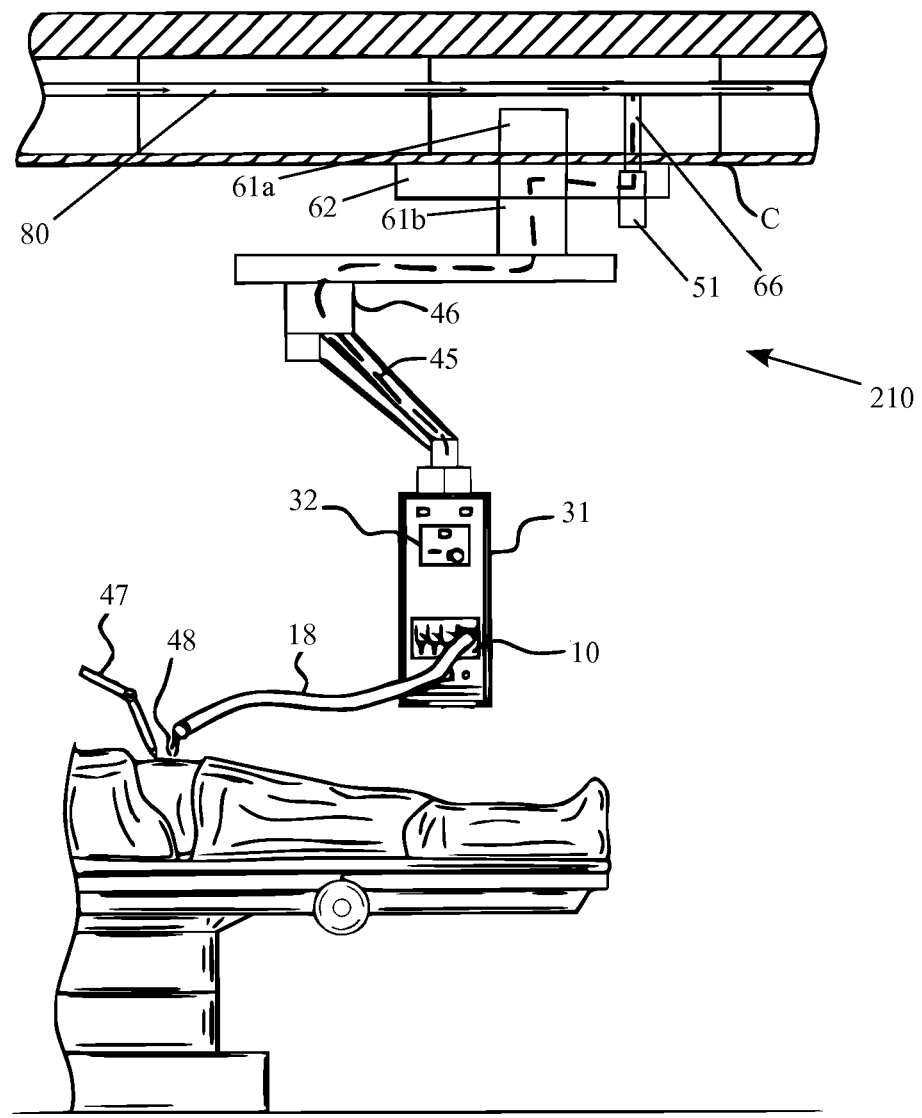
FIG. 2 shows a side view of a second embodiment filter system.
Figure 3:
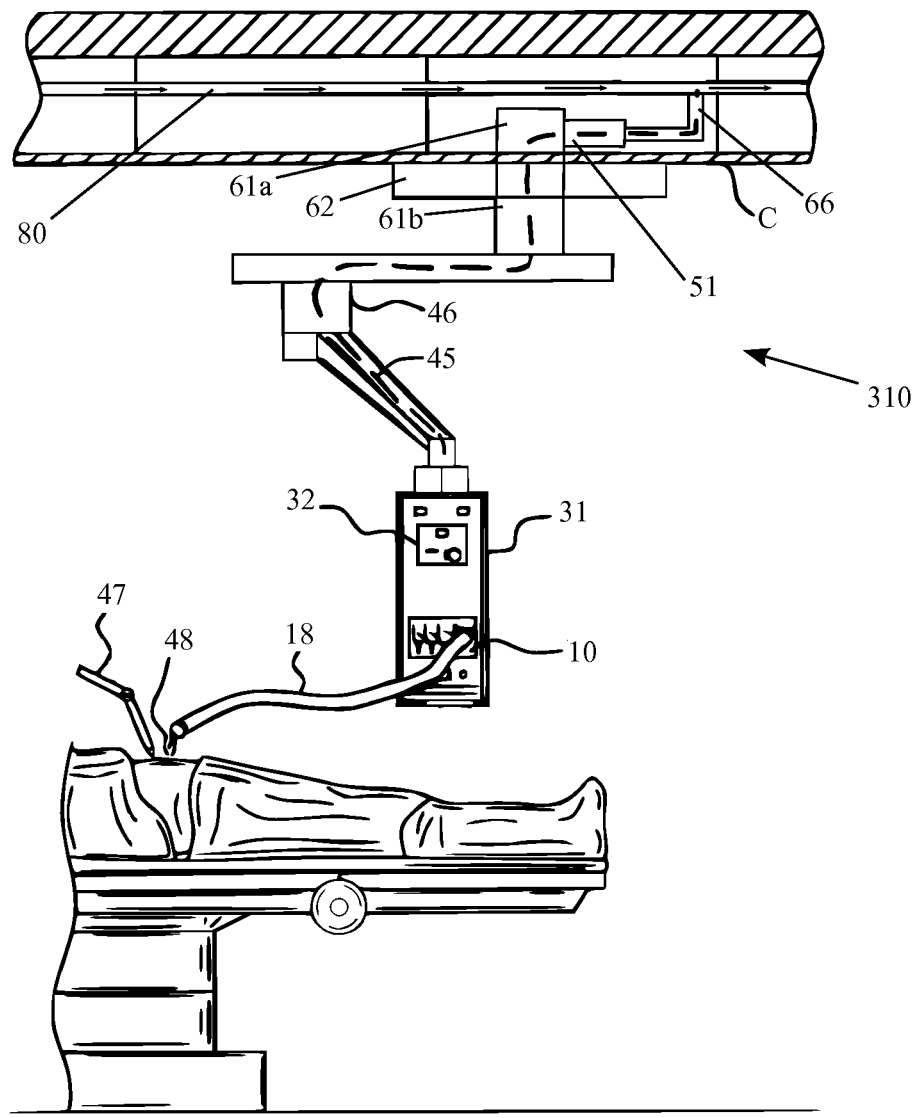
FIG. 3 shows a side view of a third embodiment filter system.
Figure 7:
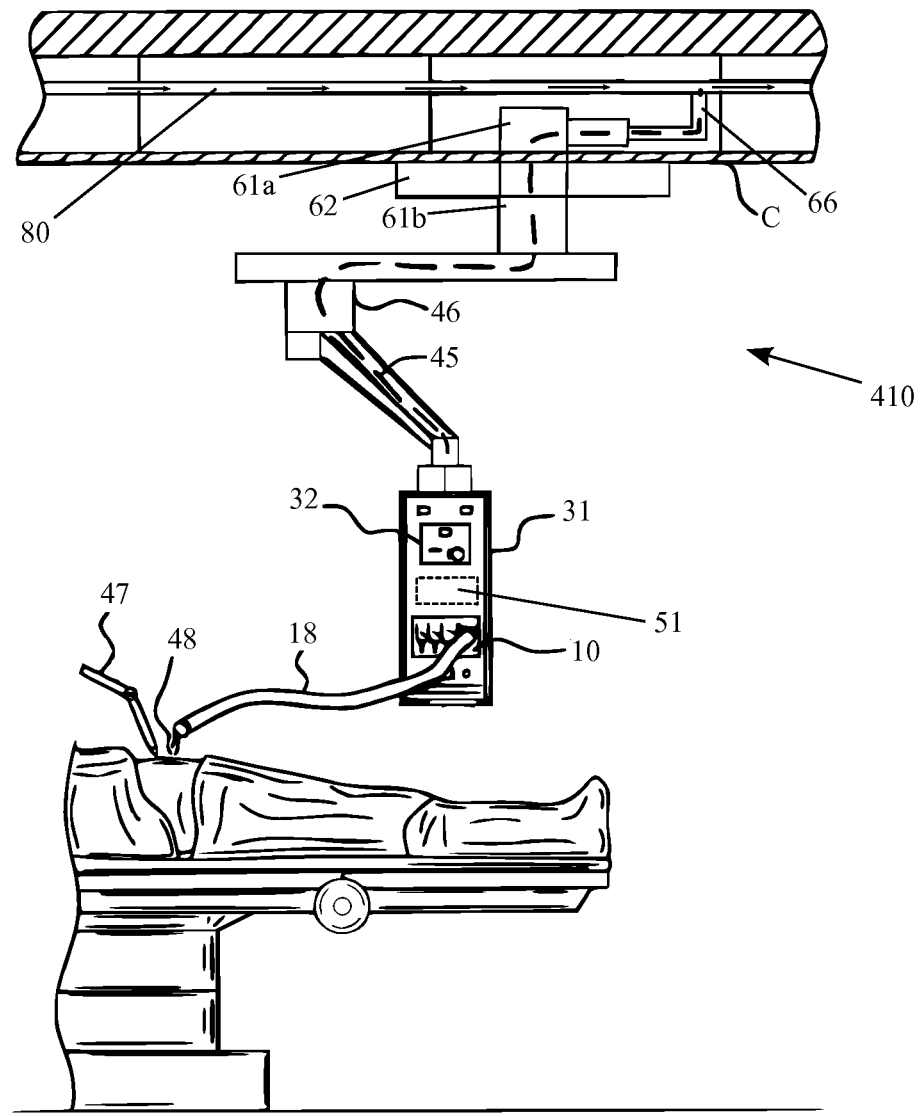
FIG. 7 shows a side view of a fourth embodiment filter system.
Figure 8:
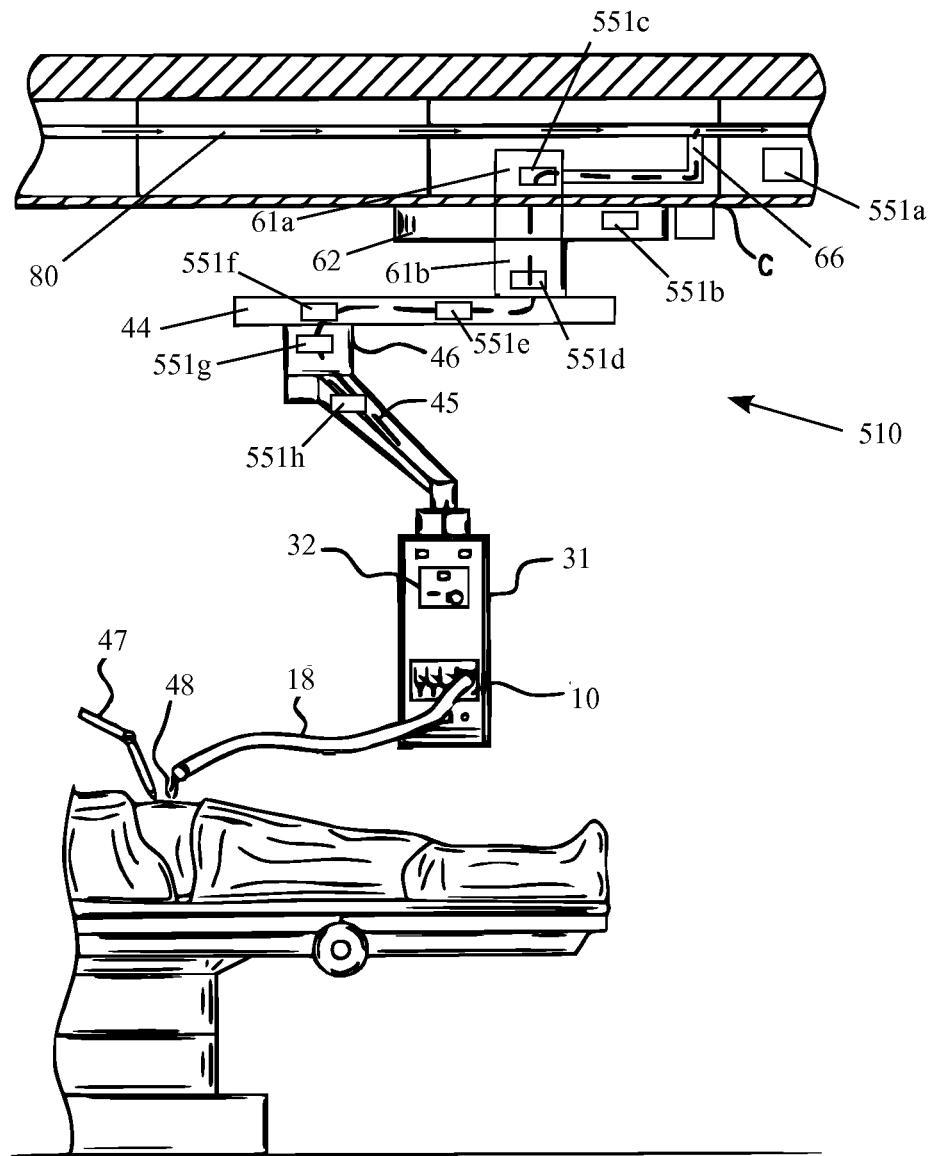
FIG. 8. shows a side view of a fifth embodiment filter system.

FIG. 2 shows a second embodiment system 210 in which suction unit 51 is mounted on collar 62. FIG. 3 shows third embodiment system 310 in which suction unit 51 is mounted on mounting shaft upper portion 61a. FIG. 7 shows a fourth embodiment system 410 in which suction unit 51 is mounted within surgical head 31 and exhaust 66 exhausting into ceiling exhaust line 80. FIG. 8 shows a fifth embodiment system in which the suction unit is arranged in several alternative locations. The suction unit may be placed at first position 551a within the ceiling adjacent to the outlet port. Alternatively, the suction unit may also be arranged in second position 551b within collar 62, third position 551c within an upper portion of shaft 61a, fourth position 551d within a lower portion of shaft 61b, fifth position 551e within a central region of horizontal linkage portion 44 of the surgical arm, sixth position 551f within a proximal region of horizontal linkage portion 44 of the surgical arm, or seventh position 551g within cylindrical joint section 46 of the surgical arm. Further, the suction unit may also be arranged at position 551h within angled descending linkage portion 45 of the surgical arm.

In the embodiment shown in FIG. 8, an RFID reader and tag pair is arranged at every coupling of the system. Fluid and suction controls, are arranged on boom portion 32. Boom portion 31 is also used to exhaust warming air.

An automatic activation system, such as described in U.S. Provisional Application No. 61/579,937 may be combined with the above embodiments to allow suction unit 51 to be activated automatically by voice, electrosurgical device sound output, electrosurgical device RF output, or a foot pedal.

The described embodiments provide a number of unexpected results and advantages over the prior art. First, by moving suction unit 51 away from service head 31, the noise in the user environment is significantly reduced. The noise and vibration from suction unit 51 has significantly increased distance to travel in order to reach the user area which results in significant attenuation in the volume of the noise had suction unit 51 been placed directly in service head 31. Additionally, having suction unit 51 separated from service head 31 resulted in decreased dust in the user area. Suction unit 51 has a certain amount of dust which escapes from it during operation and by having suction unit 51 displaced from the user area, the escaping dust is less likely from reaching the surgical area. Further, because the suction unit is not enclosed in a remote location in the ceiling, the suction unit can be easily reached for service and maintenance. The use of vibration absorbing and isolating material in the suction unit also decreased the noise and vibration experienced in the user area. The filter system also resulted in improved usability with the automatic activation unit, allowing the unit to be automatically activated by sound or RF energy and freeing a user from having to manually turn the filter on and off. The noise reducing characteristics of the filter system and the automatic activation unit synergistically worked together since the reduced noise decreased false activation of the sound activated automatic activation unit.

Therefore, while the presently-preferred form of the method and device for a remote control unit has been shown and described, and several modifications discussed, persons skilled in this art will readily appreciate that various additional changes may be made without departing from the scope of the invention.

The invention claimed is:

1. A surgical boom comprising:
   a surgical head having an electrical connection, a plurality of inlet ports, a compressed gas outlet, and a water outlet,
   one of said inlet ports having a cover,
   a hollow surgical arm mounted to a ceiling in a room and having a plurality of joints, a shaft passing through said ceiling, and a shaft collar attached to said ceiling,
   an outlet port,
   a filter media arranged between said outlet port and one of said inlet ports, said filter media comprising an ULPA media and an adsorbant layer, a control panel,
   a suction unit configured and arranged in a position below said ceiling to cause a fluid to be drawn from said inlet port through said filter media and out through said outlet port while minimizing noise in the proximity of said inlet port,
   wherein said fluid drawn from said inlet port comprises an exhaust path through said hollow arm, wherein said suction unit is arranged within a horizontal linkage portion of said arm.

2. The surgical boom as set forth in claim 1, wherein said suction unit is arranged within a proximal portion of said horizontal linkage.

3. The surgical boom as set forth in claim 1, wherein said suction unit is arranged within a distal portion of said horizontal linkage.

4. The surgical boom as set forth in claim 1, wherein said suction unit is arranged within a central portion of said horizontal linkage.

5. A surgical boom comprising:
   a surgical head having an electrical connection, a plurality of inlet ports, a compressed gas outlet, and a water outlet,
   one of said inlet ports having a cover,
   a hollow surgical arm mounted to a ceiling in a room and having a plurality of joints, a shaft passing through said ceiling, and a shaft collar attached to said ceiling,
   an outlet port,
   a filter media arranged between said outlet port and one of said inlet ports, said filter media comprising an ULPA media and an adsorbant layer, a control panel,
   a suction unit configured and arranged in a position below said ceiling to cause a fluid to be drawn from said inlet port through said filter media and out through said outlet port while minimizing noise in the proximity of said inlet port,
   wherein said fluid drawn from said inlet port comprises an exhaust path through said hollow arm, wherein said suction unit is arranged within a cylindrical joint section of said arm.

6. A surgical boom comprising:
   a surgical head having an electrical connection, a plurality of inlet ports, a compressed gas outlet, and a water outlet,
   one of said inlet ports having a cover,
   a hollow surgical arm mounted to a ceiling in a room and having a plurality of joints, a shaft passing through said ceiling, and a shaft collar attached to said ceiling,
   an outlet port,
   a filter media arranged between said outlet port and one of said inlet ports, said filter media comprising an ULPA media and an adsorbant layer,
a control panel,
a suction unit configured and arranged in a position below said ceiling to cause a fluid to be drawn from said inlet port through said filter media and out through said outlet port while minimizing noise in the proximity of said inlet port,
wherein said fluid drawn from said inlet port comprises an exhaust path through said hollow arm, wherein said suction unit is arranged within an angled descent region of said arm.

7. A surgical boom comprising:
a surgical head having an electrical connection, a plurality of inlet ports, a compressed gas outlet, and a water outlet,
one of said inlet ports having a cover,
a hollow surgical arm mounted to a ceiling in a room and having a plurality of joints, a shaft passing through said ceiling, and a shaft collar attached to said ceiling,
an outlet port,
a filter media arranged between said outlet port and one of said inlet ports,
said filter media comprising an ULPA media and an adsorbant layer,
a control panel,
a suction unit configured and arranged in a position below said ceiling to cause a fluid to be drawn from said inlet port through said filter media and out through said outlet port while minimizing noise in the proximity of said inlet port,
wherein said fluid drawn from said inlet port comprises an exhaust path through said hollow arm, wherein said suction unit is arranged within said surgical head.

8. A surgical boom comprising:
a surgical head having an electrical connection, a plurality of inlet ports, a compressed gas outlet, and a water outlet,
one of said inlet ports having a cover,
a hollow surgical arm mounted to a ceiling in a room and having a plurality of joints, a vertical shaft passing through said ceiling, and a shaft collar attached to said ceiling,
an outlet port,
a filter media arranged between said outlet port and one of said inlet ports, said filter media comprising an ULPA media and an adsorbant layer,
a control panel,
a suction unit configured and arranged in a position mounted to said shaft above said ceiling to cause a fluid to be drawn from said inlet port through said filter media and out through said outlet port while minimizing noise in the proximity of said inlet port, wherein said suction unit is arranged within said shaft at a position above said ceiling.

* * * * *